Figure 1:
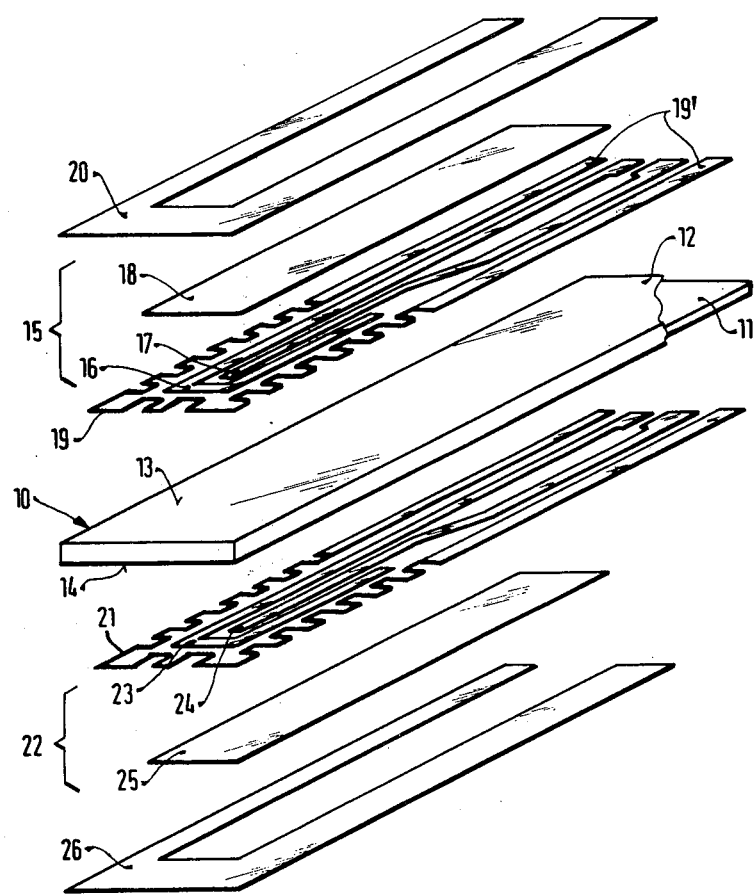

United States Patent [19]

Maurer

[11] 4,300,990
[45] Nov. 17, 1981

[54] ELECTROCHEMICAL SENSOR ELEMENT CONSTRUCTION

[75] Inventor: Helmut Maurer, Schwieberdingen, Fed. Rep. of Germany

[73] Assignee: Robert Bosch GmbH, Stuttgart, Fed. Rep. of Germany

[21] Appl. No.: 121,599

[22] Filed: Feb. 14, 1980

[30] Foreign Application Priority Data

Apr. 6, 1979 [DE] Fed. Rep. of Germany ....... 2913866

[51] Int. Cl.³ ............................................. G01N 27/58
[52] U.S. Cl. ................................................ 204/195 S
[58] Field of Search ................ 204/195 S, 1 S, 195 R; 422/98; 73/27 R

[56] References Cited

U.S. PATENT DOCUMENTS

| | | | |
|---|---|---|---|
| 3,989,614 | 11/1976 | Tien | 204/195 S |
| 4,011,538 | 3/1977 | Froemel | 73/27 R X |
| 4,045,178 | 8/1977 | Okinaka et al. | 422/98 |
| 4,193,965 | 3/1980 | Cullingford et al. | 422/95 |

FOREIGN PATENT DOCUMENTS 2826515 1/1979 Fed. Rep. of Germany .

*Primary Examiner*—G. L. Kaplan
*Attorney, Agent, or Firm*—Frishauf, Holtz, Goodman & Woodward

[57] ABSTRACT

To improve uniformity of heating of a sensor element carried on a plate-like carrier, in which electrodes are applied to one or both of the major surfaces of a carrier plate to form the sensor element, the heater element is constructed in form of a zig-zag or meander track surrounding the flat electrodes and positioned adjacent the edge portion of the carrier plate, so that, in a direction transverse to the major plane of the carrier plate, the heater element will be positioned closely adjacent the electrode, and prevent the formation of temperature gradients which might lead to fissures or breaks in the elements of the sensor construction.

10 Claims, 3 Drawing Figures

ELECTROCHEMICAL SENSOR ELEMENT CONSTRUCTION

REFERENCE TO RELATED PUBLICATIONS

German Disclosure Document DE-OS No. 28 26 515, German Disclosure Document DE-OS No. 28 15 879 (to which U.S. Pat. No. 4,193,965, Cullingford et al, and claiming the same priority, corresponds) U.S. Pat. No. 3,989,614, Tien, U.S. Ser. No. 121,598, filed Feb. 14, 1980, MULLER et al U.S. Ser. No. 121,600, filed Feb. 14, 1980, MULLER et al, U.S. Ser. No. 121,632, filed Feb. 14, 1980, MULLER et al said applications being assigned to the assignee of this application.

The present invention relates to an oxygen sensor construction, and more particularly to such a sensor construction which is suitable for incorporation into an oxygen sensor to determine the oxygen content of gases resulting from a combustion process, and especially of exhaust gases from automotive-type internal combustion engines.

BACKGROUND AND PRIOR ART

Various types of sensors have been proposed in which a carrier plate for a sensor element is provided and on which, further, a heating element is applied in order to heat the carrier plate, and with it the sensor element, to a suitable operating temperature—see the Referenced German Disclosure Documents DE-OS Nos. 28 26 515, and 28 15 879 (to which U.S. Pat. No. 4,193,965, Cullingford et al corresponds) and also U.S. Pat. No. 3,989,614, T. Y. Tien. The heating elements of those sensors are applied to one side of the major plane of a carrier plate, the other side of the major plane of the carrier plate carrying the sensor element as such. The plate is placed in a stream of combustion exhaust gases. As hot combustion gases pass by the sensor, the temperature of the sensor element itself shows a gradient between the outer edge zones and the central zone. The central zone which is directly impinged by the hot gases will have a higher temperature than the outer end zones. As a consequence of the temperature gradient within the sensor element itself, output signal variations will be observed although there is no change in the gas composition; further, the delicate sensor structure itself, and also the carrier support therefor, is subject to fracture, leading to loss of a control signal from the sensor.

THE INVENTION

It is an object to provide a sensor construction in which temperature gradients are eliminated or, at least, reduced to such an extent that the output signal will be more uniform, and damage to the sensor element itself due to temperature gradients can be avoided.

Briefly, the sensor element is applied to the same face of the support plate or carrier plate as the heating element, the heating element surrounding the sensor element at the outside thereof; the structure is so arranged that, in a vertical projection transverse to the major plane of the carrier plate, the heating element surrounds at least two sides, and preferably three sides of the flat or layer-like sensor element, and is positioned closely adjacent thereto.

The structure has the advantage that the heater element or the elements will provide heat to the sensor elements over an area which will result in essentially uniform, balanced thermal conditions and which counteract the tendency of the carrier plate to fracture. The structure is suitable for mass production, and especially if, in accordance with a feature of the invention, the heating element, in the region of the sensor element, is located in a meander or zig-zag arrangement. Two heating elements may be provided, one on each plane or flat side of the carrier plate, the carrier plate itself forming either an active or an inactive structural component of the sensor element.

Figure 2:
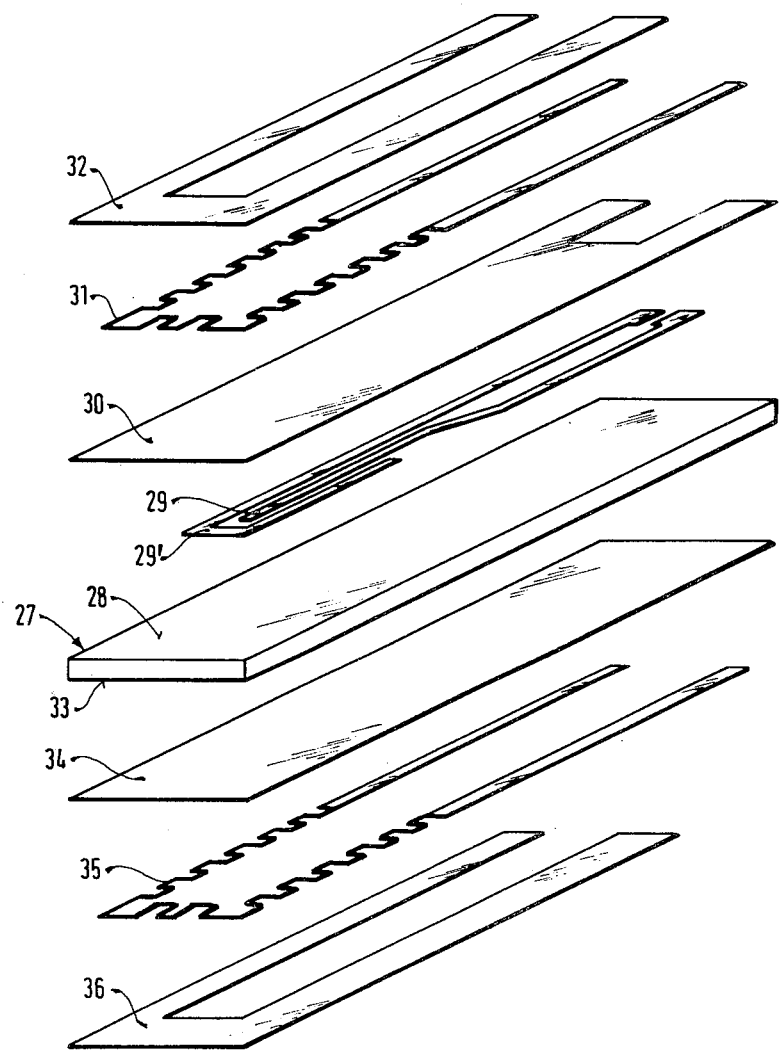
Figure 3:
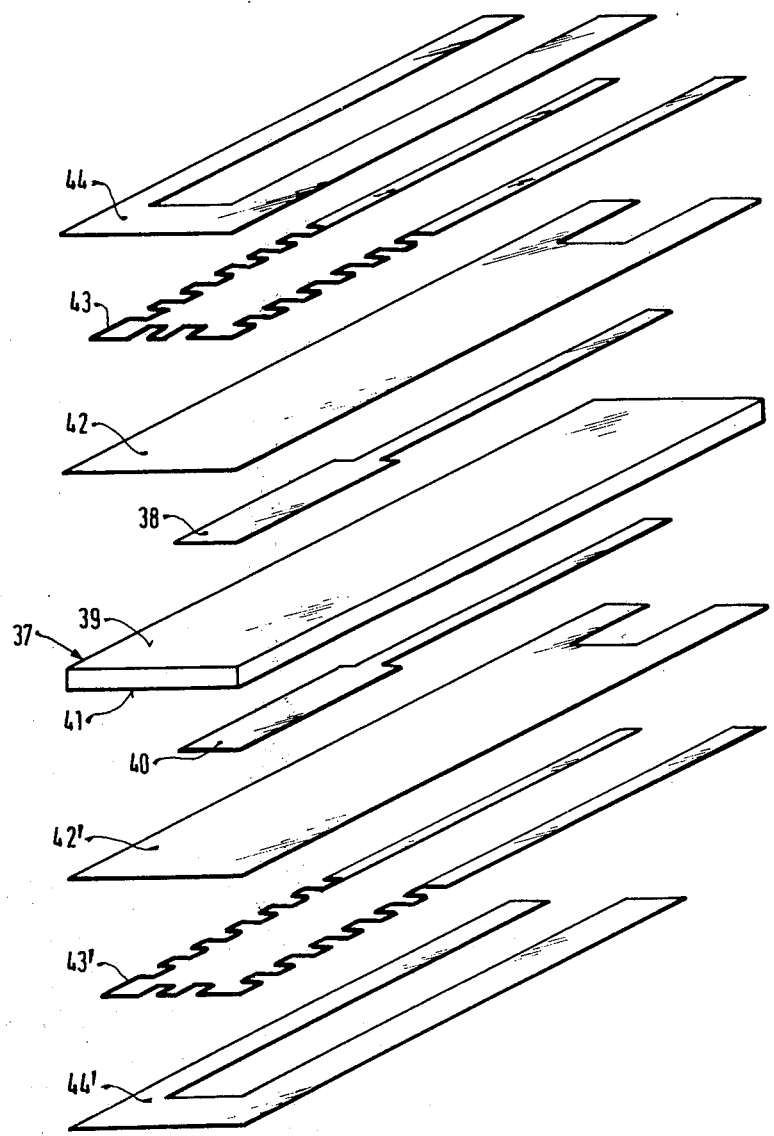

Drawings, illustrating an example, wherein:

FIG. 1 is an exploded perspective view of an inactive sensor carrier plate having, on each one of its major sides, a sensor element and a heater element applied thereto, and illustrated to a greatly enlarged scale;

FIG. 2 is an exploded view of a carrier plate which forms an active component of the sensor applied to one of its major sides and having a heater element on each one of its major sides; and FIG. 3 is a highly enlarged exploded view of a carrier plate which forms an active part of the sensor and which has an electrode, each, of the sensor element on one of its major sides and a heating element on each side thereof.

The sensor of FIG. 1, when assembled together, can be inserted in a housing of any known or suitable construction, for example as shown in the referenced co-pending applications, or in structures in accordance with patents referred to therein or structures disclosed in the referenced published German Disclosure Documents. FIG. 1 shows a carrier plate 10 which is a composite formed of a metal plate 11 and a ceramic cover 12. The metal plate 11 may, for example, be a structural support plate formed of a heat resistant nickel alloy, for example about 5 mm wide and 0.6 mm thick. The ceramic cover is an aluminum oxide layer 12 of about 0.5 mm thickness. Other carrier plates 10 can be used, for example the carrier plate 10 can be a single solid electrically insulating ceramic.

The sides forming major planes or surfaces of the carrier plate are shown at 13 and 14. Major plane 13 has a potentiometric sensor 15 applied thereto to determine oxygen contents of a gas impinging thereon—for example the exhaust gas of an internal combustion engine—and includes a sensing electrode 16, a reference electrode 17, and an oxygen ion conductive solid electrolyte layer 18, for example made of zirconium dioxide, and of about 0.5 mm thickness and forming a sensor element. The sensing electrode 16 is a layer of a platinum metal of about 7 μm thickness; the reference electrode 17 is a layer of gold of about the same thickness. Both electrodes 16, 17 are exposed to the gas to be measured. The sensing electrode 16 and the reference electrode 17 are connected to or extended by conductive paths or tracks to the end portion of the sensor remote from the portion which is exposed to the gases, for connection to a suitable evaluation circuit. The oxygen sensor operates in the form of an electrochemical cell and provides an output voltage which depends on the oxygen partial pressure of the gas to be sensed, the output voltage forming the signal representative of the oxygen within the gas.

In accordance with the invention, the electrodes 16, 17 take up less of the flat space of the surface 13 of plate 10 than provided by the plate 10, leaving edge strips along the longitudinal and end portions of the surface 13. A heater element 19 which, for example, is in form of a track of platinum, is applied to the same surface as the sensing unit 16, 17, 18. The platinum track 19 has a thickness of about 10 μm, and is applied, just like the electrode 16 and/or the reference electrode 17 in accordance with any suitable and well known process of film technology, such as printing, spraying-on, vapor deposition, or the like. Preferably, the heater element 19 is arranged in a meander or zig-zag configuration, and applied as close to the sensor element 15 as possible, being, however, electrically insulated therefrom. It essentially surrounds the sensor element 15 over a major portion thereof, at least on two and, as shown, three sides. The heater element 19 fills the edge strip or zone in its entire width. The heater element 19 is extended by conductive tracks 19' to the terminal end portion of the carrier plate 10, that is, the portion remote from the sensing electrodes. To protect the heater element against oxidation, and against destruction by the hot exhaust gases, a cover layer 20 is applied thereover. Cover layer 20 is an electric insulator, for example of aluminum oxide.

The heater element 19 ensures that the region of the sensor element 15 is heated approximately uniformly. Consequently, the output signals from the sensor element 15 will be reliably representative of the oxygen content of the gas impinging on the sensor. The edge portions of the carrier plate 10, which is thermally loaded most by gases flowing thereabout, is protected against fissures and breakage.

The thermal condition of the sensor element 15 can be still further improved and stabilized if, as is desirable for some applications, the other flat side 14 of the sensor plate 10 has an additional heater element 21 applied thereto. Heater element 21 can extend over the entire width of the carrier plate 10; it may, however, and as shown in FIG. 1, be of equal configuration and arrangement as the heater element 19. Heater element 21 is protected and covered by a cover 26, similar to the cover 20. If a heater element 21 is used which has the same arrangement as the heater element 19, it is possible to apply an additional sensor element 22 in the region surrounded by the heater element 21 on the carrier plate 10. The additional sensor element 22 may be a potentiometric sensor similar to sensor 15 or it may be a polarographic oxygen sensor, that is, a sensor which is connected externally to a source of voltage and in which the current flow is representative of oxygen content of the gas to which it is exposed. The polarographic sensor 22 has a measuring electrode 23 and a reference electrode 24 located adjacent thereto. Both electrodes 23, 24 can be of platinum or a platinum metal and are exposed to the gas to be tested. They can be applied to the carrier plate 10 together with the heater element 21 by a any suitable and known process, together with the conductive paths or tracks extending to the terminal end portion of the sensor. The electrodes 23, 24 are covered with a solid electrolyte layer 25 which is oxygen ion conductive and pervious to oxygen molecules. Layer 25, for example, is about 0.6 μm. The electrodes 23, 24 are connected to an electrical voltage and the sensor 22, 23, 24 then provides an output current which will depend on the oxygen content in the gas to which the sensor is exposed. Rather than using a polarographic sensor 22–24 or, in addition to the polarographic sensor 22–24, other sensors can be applied to the carrier plate 10, for example a temperature sensor, a carbon or soot sensor, or the like; the particular type of additional sensor which is applied to the obverse side 14 of the plate 10 does not form part of the present invention and, therefore, a detailed description thereof is not provided. Application of any one of the other sensors to a carrier element, by themselves, is well known.

Each one of the heating elements 19, 21 can be supplied from an individual controlled current source so that the respective sensors 15-and/or 22 can be individually and precisely heated, for example as determined by a temperature sensor additionally positioned adjacent to the electrodes, or therebetween, or at another suitable location on the carrier plate 10.

The carrier plate 10 and sensor elements 15, 22 as well as the heater elements 19, 21, can be secured reliably and tightly in the longitudinal opening of a metal housing, for example as described in U.S. Pat. No. 3,989,614, Tien.

Embodiment of FIG. 2: A solid carrier plate 27, for example itself consisting of oxygen ion conductive solid electrolyte material such as zirconium dioxide, has a thickness of about 0.8 mm and forms an active component of the oxygen ion sensor described, for example, in the embodiment of FIG. 1. The upper side 28 of the carrier plate 27 has an electrode pair 29, 29' and associated conductive tracks applied thereto, extending from the sensing portion at the left (FIG. 2) end of the sensor element to the connecting portion at the right thereof. The portion of the solid electrolyte material of plate 27 between the electrodes 29, 29' forms the sensor element. The marginal end portions of surface 28 are left uncovered. An electrically insulating, but oxygen ion pervious, cover 30 is applied over the electrode pair 29, 29' which has a cut-out at the terminal end portions to permit the formation of an electrical connection to the conductive tracks. The cover 30 may, for example, be made of aluminum oxide. A heater element 31 is so applied thereto that its vertical projection—transverse to the plane 28 of carrier plate 27—falls in the edge region not covered by the electrode pair 29, 29' of the carrier plate 27—prefereably covering the entire edge region. Partial overlap of the electrode pair 29, 29' by the heater element 31 may be of advantage in certain arrangements. Heater element 31 is extended with conductive tracks towards the terminal end portions of the sensor element and is covered with a protective cover 32 preventing oxidation of heater element 31. Cover 32 is slightly shorter than the plate 28 to leave the terminal ends of the conductive tracks free for connection to a current source to heat the sensor heater 31.

The lower side 33 of carrier plate 27 has an electrically insulating layer 34, for example aluminum oxide, applied thereto, and a heater element 35 is applied to its edge region. Heater element 35 is extended with conductive tracks towards the terminal portion of the sensor element. A protective cover 36 is applied over the heater element 35, protecting it against the hot exhaust gases. The portion of the surface of side 33 can receive another sensor, if desired. If no other sensor is applied in this region, then the thermal equilibrium of the sensor is improved if the heater element 35 is used as shown, rather than a heater element which extends over the entire surface of the plate 33. The additional sensor within the heater element 35 need not be an oxygen sensor but, as referred to above, may be a temperature sensor, a soot detector, or the like. All other elements and features of the embodiment of FIG. 2 are similar to those of FIG. 1.

Embodiment of FIG. 3: An oxygen ion sensor has a carrier plate 37 which corresponds to the carrier plate 27 (FIG. 2), that is, is of a solid electrolyte ion conductive material. The sensor element electrode 38 which is applied to the upper side 39 of plate 37 forms one electrode. The counter electrode 40 is applied to the other side 41 of the plate 37. The portion of plate 37 between the electrodes 38,40 forms the sensor element. Both electrodes 38, 40 are covered with a protective cover 42, 42'—similar to cover 30, FIG. 2—and a heater element 43, 43', respectively, is applied to the covers 42, 42'. Outer protective layers 44, 44' protect the respective heater elements 43,43'. In all other respects, the sensor is similar to those previously described.

The embodiments of FIGS. 2, 3 illustrate the versatility of the present invention, and the various uses and different applications with which it may be utilized.

The carrier plate 37 forms an active part of the sensor, and each one of the major sides 39, 41 has an electrode 38, 40 applied thereto. This sensor can also be used with the type of oxygen sensor in which one of the electrodes, for example electrode 40, is exposed to a reference substance having a predetermined oxygen partial pressure, for example oxygen of ambient air, or oxygen derived from a metal-metal oxide mixture such as, for example, nickel/nickel oxide or iron/iron oxide. If the electrode 40 is to be used as a reference electrode, it should be suitably encapsulated, the encapsulating either retaining an oxygen partial pressure supplying substance or being connected to ambient air. Reference is made to copending application Ser. No. 121,632, filed Feb. 14, 1980, MULLER et al, assigned to the assignee of this application, which illustrates a suitable structure to encapsulate an electrode and provide a reference oxygen level thereto.

Various changes and modifications may be made, and features described in connection with any one of the embodiments may be used with any of the others, within the scope of the inventive concept.

I claim:

1. Electrochemical sensor construction adapted for positioning in a stream of combustion gases, having
    a plane carrier plate (10, 27, 37) with two opposed sides, each defining a flat surface;
    at least one planar sensor element (15, 22; 27, 29, 29'; 37, 38, 40) supported on the carrier plate, positioned against one flat surface and having a plan outline smaller than said one surface, leaving marginal portions of said one surface of the carrier plate extending beyond the sensor element;
    and a planar heating element (19, 21; 32, 35; 43, 43') supported on the carrier plate;
    wherein, the heating element is positioned on at least one of the sides of the plate, placed to laterally surround at least one sensor element about a major portion thereof and located closely adjacent thereto, the heating element being positioned adjacent to and at least one sensor element, and electrically insulated from the at least one sensor element; and
    the sensor element occupies a portion centrally on the carrier plate with respect to the lateral dimension thereof—and the heating element is positioned at the edge side and end portions.

2. Construction according to claim 1, wherein the heater element (19, 21; 31; 43, 43') supported on the carrier plate (10, 27, 37) is arranged in zig-zag or meander configuration in the region of the sensor element (15, 22; 27, 29, 29'; 37, 38, 40).

3. Construction according to claim 1, wherein the heater element (19, 21, 31) is positioned on the same side (13, 14, 28) of the carrier plate (10, 27) as the sensor element (15, 22; 27, 29, 29').

4. Construction according to claim 1, wherein each one of the flat sides (13, 14; 28, 33; 39, 41) of the carrier plate (10, 27, 37) has a heating element supported thereby.

5. Construction according to claim 1, wherein (FIG. 1) the carrier plate (10) is an inactive support plate for at least one sensor element (15, 22).

6. Construction according to claim 1, wherein at least one sensor element (27, 29, 29'; 37, 38, 40) comprises a portion of the carrier plate (27, 37), and said portion of the carrier plate forms a component of the sensor construction.

7. Construction according to claim 1, wherein at least one of the sensor elements (15, 22; 27, 29, 29'; 37, 38, 40) to be heated includes an oxygen ion conductive solid electrolyte material.

8. Construction according to claim 7, wherein the electrolyte material comprises zirconium dioxide.

9. Construction according to claim 1, wherein the heating element is positioned in a plane different from that of the sensor element;
    and the heater element overlaps a portion of the sensor element.

10. Construction according to claim 1, wherein the heater element and the at least one sensor element are positioned in essentially the same plane, and the heater element and the at least one sensor element are located adjacent, but laterally spaced and insulated from each other.

* * * * *